(12) United States Patent
Aichinger et al.

(10) Patent No.: US 7,601,512 B2
(45) Date of Patent: Oct. 13, 2009

(54) METHODS FOR IDENTIFYING INHIBITORS OF THE 20S AND 26S PROTEASOME

(75) Inventors: Christian Aichinger, München (DE); Peter Schreier, Köln (DE); Ronald Ebbert, Monheim (DE); Robert Huber, Germering (DE); Michael Groll, Bad Füssing (DE)

(73) Assignee: Bayer CropScience AG, Monheim (DE)

( * ) Notice: Subject to any disclaimer, the term of this patent is extended or adjusted under 35 U.S.C. 154(b) by 539 days.

(21) Appl. No.: 10/621,866

(22) Filed: Jul. 17, 2003

(65) Prior Publication Data
US 2004/0053312 A1 Mar. 18, 2004

(30) Foreign Application Priority Data
Jul. 19, 2002 (DE) ............................... 102 32 902

(51) Int. Cl.
*C12Q 1/68* (2006.01)
*C12Q 1/18* (2006.01)
(52) U.S. Cl. ..................... 435/32; 435/7.91; 435/7.71
(58) Field of Classification Search ...................... None
See application file for complete search history.

(56) References Cited

U.S. PATENT DOCUMENTS

| | | | | |
|---|---|---|---|---|
| 5,425,942 A | 6/1995 | Tanaka | ...................... | 424/94.1 |
| 5,693,617 A | 12/1997 | Stein et al. | ..................... | 514/18 |
| 6,613,541 B1 | 9/2003 | Vaddi et al. | .................... | 435/23 |

FOREIGN PATENT DOCUMENTS

| | | |
|---|---|---|
| CA | 2077665 | 9/1991 |
| CA | 2 359 561 | 7/2001 |
| JP | 5-292964 | 11/1993 |
| JP | 6-22759 | 2/1994 |
| WO | 98/42829 | 10/1998 |
| WO | WO 00/23614 A1 * | 4/2000 |

OTHER PUBLICATIONS

Science, vol. 268, May 5, 1995, pp. 726-731, "Inhibition of Proteasome Activities and Subunit-Specific Amino-Terminal Threonine Modification by Lactacystin" by G. Fenteany et al.
Nature, 386, Apr. 3, 1997, pp. 463-471, "Structure of 20S proteasome from yeast at 2.4 Å resolution" by M. Groll et al.
Journal of Biomolecular Screening, vol. 4, No. 2, (month unavailable) 1999, pp. 67-73, "A Simple Statistical Parameter for Use in Evaluation and Validation of High Throughput Screening Assays" by Ji-Hu Zhang et al.
Chem. Biol. 5, (month unavailable) 1998, pp. 307-320, "Substrate binding and sequence preference of the proteasome revealed by active-site-directed affinity probes" by M. Bogyo et al.
Annu. Rev. Biochem., 65, (month unavailable) 1996, pp. 801-847, "Structure And Functions Of The 20S and 26S Proteasomes" by O. Coux et al.

J. Biol. Chem., 273 (15), Apr. 10, 1998, pp. 8820-8828, "Enzymes Catalyzing Ubiquitination and Proteolytic Processing of the p105 Precursor of Nuclear Factor κB1" by O. Coux et al.
J. Biol. Chem., 265, Mar. 25, 1990, pp. 4789-4792, "The Proteasome (Multicatalytic Protease) Is a Component of the 1500-kDa Proteolytic Complex Which Degrades Ubiquitin-conjugated Proteins" by J. Driscoll et al.
Proc. Natl. Acad. Sci. USA, vol. 96, pp. 10403-10408, Aug. 1999, "Epoxomicin, a potent and selective proteasome inhibitor, exhibits in vivo antiinflammatory activity" by L. Meng et al.
Bioscene, 26 (3), (month unavailable) 2000, pp. 9-13, "Modeling Antimicrobial Activity of Clorox™ Using an Agar-Diffusion Test: A New Twist on an Old Experiment" by J. K. Mitchell et al.
Biochemistry, (month unavailable) 1993, 32, pp. 1563-1572, "Evidence for the Presence of Five Distinct Proteolytic Components in the Pituitary Multicatalytic Proteinase Complex. Properties of Two Components Cleaving Bonds on the Carboxyl Side of Branched Chain and Small Neutral Amino Acids" by M. Orlowski et al.
Cell, vol. 60, pp. 295-306, Jan. 26, 1990, "The *b* Alleles of *U. maydis*, Whose Combinations Program Pathogenic Development, Code for Polypeptides Containing a Homeodomain-Related Motif" by B. Schulz et al.
Nature Biotechnology, Dec. 18, 2000, pp. 1298-1302, "A ubiquitin-based tagging system for Controlled modulation of protein stability" by J. H. Stack et al.
Biochemistry, (month unavailable) 1996, 35, pp. 3899-3908, "Kinetic Characterization of the Chymotrypic Activiity of the 20S Proteasome" by R. L. Stein et al.
Neuroscience Letters, 201, (month unavailable) 1995, pp. 29-32, "Calpain inhibitor I decreases βA4 secretion from human embyonal kidney cells expressing β-amyloid precursor protein carrying the APP670/671 double mutation" by Hans-W. Klafki et al.
Nature, 390, Dec. 1997, pp. 639-643, "Structure of the proteasome activator REGα (PA28α)" by J. Randolph Knowlton et al.
Chem Biol., 6, (month unavailable) 1999, pp. 689-698, "The secondary fungal metabolite Gliotoxin targets proteolytic activities of the proteasome" by M. Kroll et al.
Molecular And Cellular Biology, vol. 18, Jan. 1998, pp. 30-38, "Proteasome Inhibitors Cause Induction of Heat Schock Proteins and Trehalose, Which Together Confer Thermotolerance in *Saccharomyces cerevisiae*" by Do Hee Lee et al.
The Journal Of Biological Chemistry, vol. 271, No. 44, Issue of Nov. 1, 1996, pp. 27280-27284, "Selective Inhibitors of the Proteasome-dependent and Vacuolar Pathways of Protein Degradation in *Saccharomyces cerevisiae*" by Do Hee Lee et al.
The Journal Of Biological Chemistry, vol. 272, No. 47, Issue of Nov. 21, 1997, pp. 29899-29903, "Specificities of Cell Permeant Peptidyl Inhibitors for the Proteinase Activities of μ-Calpain and the 20 S Proteasome" by R. L. Mellgren.

(Continued)

Primary Examiner—Robert A Zeman
(74) Attorney, Agent, or Firm—Raymond J. Harmuth; Richard E. L. Henderson

(57) ABSTRACT

The present invention relates to methods for identifying fungicides and also inhibitors of the 20S and 26S proteasomes, to methods for isolating 20S proteasomes, to the use of 20S proteasomes for identifying fungicides and to the use of the inhibitors of 26S and/or 20S proteasomes as fungicides.

2 Claims, 7 Drawing Sheets

OTHER PUBLICATIONS

Biochemistry, (month unavailable) 1998, pp. 7792-7800, "Kinetic Studies of the Branched Chain Amino Acid Preferring Peptidase Activity of the 20S Proteasome: Development of a Continuous Assay and Inhibition by Tripeptide Aldehydes and *clasto*-Lactacystin β-Lactone" by T. A. McCormack et al.

Jones R. W. et al: "Variation in Sensitivity Among Anastomosis Groups of Rhizoctonia-Solani To The Antibiotic Gliotoxin" Plant Disease, Bd. 71, Nr. 1, 1987, Seiten 34-36, XP009019179 ISSN: 0191-2917 das ganze Dokument.

Saeki Yasushi et al: "Rapid isolation and characterization of the yeast proteasome regulatory complex" Biochemical and Biophysical Research Communications, Bd. 273, Nr. 2, Jul. 5, 2000, Seiten 509-515, XP002268381.

Emmerlich Vera et al: "Isolation and subunit composition of the 20S proteasome of *Giardia lamblia*" Molecular and Biochemical Parasitology, Bd. 100, Nr. 1, May 15, 1999, Seiten 131-134, XP002268382.

Hori Hiroshi et al: "Isolation and characterization of two 20S proteasomes from the endoplasmic reticulum of rat liver microsomes" Journal of Biochemistry (Tokyo), Bd. 126, Nr. 4, Oct. 1999, Seiten 722-730, XP009019175.

Furet P. et al: "Modeling of the Binding Mode of a Non-Covalent Inhibitor of the 20S Proteasome. Applications to Structure-Based Analogue Design" Bioorganic & Medicinal Chemistry Letters, Oxford, GB, Bd. 11, Nr. 10, May 21, 2004, Seiten 1321-1324, XP001059888.

Koguchi Y. et al: "TMC-95A, B, C and D, Novel Proteasome Inhibitors Produced by Apiospora Montagnei Sacc. TC 1093 Taxonomy, Production, Isolation and Biological Activities" Journal of Antibiotics, Japan Antibiotics Research Association. Tokyo, JP, Bd. 53, Nr. 2, Feb. 2000, Seiten 105-109, XP002953124.

* cited by examiner

SEQUENCE LISTING

```
<160> NUMBER OF SEQ ID NOS: 2

<210> SEQ ID NO 1
<211> LENGTH: 4
<212> TYPE: PRT
<213> ORGANISM: Artificial Sequence
<220> FEATURE:
<223> OTHER INFORMATION: Substrate for 20S proteasome
<220> FEATURE:
<221> NAME/KEY: MOD_RES
<222> LOCATION: (1)..(1)
<223> OTHER INFORMATION: N-succinyl residue
<220> FEATURE:
<221> NAME/KEY: MOD_RES
<222> LOCATION: (4)..(4)
<223> OTHER INFORMATION: 7-amino-methylcoumarin residue

<400> SEQUENCE: 1

Leu Leu Val Tyr
1

<210> SEQ ID NO 2
<211> LENGTH: 4
<212> TYPE: PRT
<213> ORGANISM: Artificial Sequence
<220> FEATURE:
<223> OTHER INFORMATION: Inhibitor of proteasome
<220> FEATURE:
<221> NAME/KEY: MOD_RES
<222> LOCATION: (1)..(1)
<223> OTHER INFORMATION: N-carbobenzyloxycarbonyl residue
<220> FEATURE:
<221> NAME/KEY: MOD_RES
<222> LOCATION: (2)..(2)
<223> OTHER INFORMATION: OtBu residue
<220> FEATURE:
<221> NAME/KEY: MOD_RES
<222> LOCATION: (4)..(4)
<223> OTHER INFORMATION: CHO residue

<400> SEQUENCE: 2

Ile Glu Ala Leu
1
```

METHODS FOR IDENTIFYING INHIBITORS OF THE 20S AND 26S PROTEASOME

BACKGROUND OF THE INVENTION

The present invention relates to methods for identifying fungicides and also inhibitors of the 20S and 26S proteasomes, to methods for isolating 20S proteasomes, to the use of 20S proteasomes for identifying fungicides and to the use of the inhibitors of 26S and/or 20S proteasomes as fungicides. Although abbreviated citations are used hereinafter for convenience, the full citation of any abbreviated citation is available in the References section of this specification.

Undesired fungal growth which leads to considerable damage in agriculture every year, for example, can be controlled by the use of fungicides. The demands made on fungicides have increased constantly with regard to their activity, their costs and above all their ecological soundness. There exists therefore a demand for novel substances or classes of substances which can be developed into potent and ecologically sound novel fungicides. In general, it is customary to search for such novel lead structures in greenhouse tests. However, such tests are labour-intensive and expensive. The number of substances which can be tested in a greenhouse is, accordingly, limited. An alternative to such tests is the use of "high-throughput screening" (HTS) methods. This involves testing a large number of individual substances with regard to their effect on cells, individual gene products or genes in an automated method. When certain substances are found to have an effect, they can be studied in conventional screening methods and, where appropriate, developed further.

Ideal fungicides are, for example, those substances which inhibit gene products which have a decisive importance in the manifestation of the pathogenicity of a fungus. An example of such a fungicide is the active compound carpropamid which inhibits fungal melanin biosynthesis and thus prevents the formation of intact appressoria (adhesion organs). However, there is only a very small number of known gene products playing such a part in fungi. In addition, fungicides are known which lead to auxotrophism of the target cells by inhibiting corresponding biosynthetic pathways and, consequently, to the loss of pathogenicity.

Other important starting points are polypeptide or polypeptide complexes which play a central part in essential cellular processes or essential protein activities. The emphasis here is on the inhibition of enzymic reactions but it is also possible to inhibit the interaction of proteins or the functional interaction of complex protein machinery.

An example of such a complex "protein machinery" which is at the centre of cellular processes is the 26S proteasome. The biological function of the 26S proteasome comprises a multiplicity of functions, inter alia degradation of misfolded and misassembled proteins and peptides, regulation of stress response by, for example, degradation of transcription factors, or cell cycle control by the degradation of cyclins. For the cellular immune response, peptides are processed in such a way that they can be presented subsequently on the outer surface by the MHC I complex. The catalytic core of the 26S proteasome is the 20S proteasome. The 20S proteasome itself has various peptidase activities on which the enzymic activity of the 20S proteasome is based, as a result of which the 20S proteasome, in particular is an interesting target for substances which influence the said enzymic activities.

The proteolytic activity of the proteasome in vivo requires ubiquitination of the target proteins and consumes ATP. In this connection, the target proteins are degraded by transferring ubiquitin onto the target protein. The ubiquinated protein is then transported to the proteasome, where it is degraded and the ubiquitin is recycled.

It is known that all proteins of the 20S proteasome, except one in *S. cerevisiae*, are necessary for cell growth. The complex comprises a plurality of different proteolytic activities such as, for example, a peptidyl-glutamyl peptide-hydrolysing (PGPH) activity, a tryptic and a chymotryptic activity. Mutational analyses have revealed that the chymotryptic activity is the most important one in the complex. Previously, it has not been possible to express the 20S proteasome heterologously, but native purification of active 20S proteasomes from yeast have already been described.

The term "enzymic activity" of the 20S or 26S proteasome, as used herein, refers to at least one of the various enzymic activities of the 20S or 26S proteasome. Accordingly, an "enzymically active" 20S or 26S proteasome is still capable of carrying out at least one of the naturally occurring enzymic reactions.

The eukaryotic 26S proteasome consists of in each case one proteolytic and two regulatory complexes. The 20S proteasome is composed of 7 different α- and seven different β-subunits which have already been cloned from various organisms and sequenced. The 20S proteasome from baker's yeast (*S. cerevisiae*) has a molecular weight of approx. 700 kD. Likewise, various publications have already described the purification of proteasomes from eukaryotes (e.g. WO 98/42829 A1; EP 0 345 750 A2). The efforts to purify proteasomes in the best possible way finally also resulted in resolving of the structure of the 20S proteasome from *S. cerevisiae* (WO 98/42829 A1; Groll et al. (1997), Structure of the 20S proteasome from yeast at 2.4 Å resolution, *Nature* 386, 463-471).

Coux et al. (1998), (Enzymes catalyzing ubiquitination and proteolytic processing of the p105 precursor of nuclear factor kappaB1. *J. Biol. Chem.* 273(15), 8820-8828) describe the multiple proteolytic activities of the 20S proteasome as chymotrypsin-like, trypsin-like, PGPH, and as preferring branched amino acid chains and small neutral amino acids. The proteolytic activity can be enhanced by various induction conditions. These include, for example, heating the proteasome to 55° C. or the addition of SDS. Moreover, McCormack et al. (1998), *Biochemistry* 37, 7792-7800 describe various substrates for detecting the proteolytic activity of the 20S proteasome, such as, for example, Suc-Leu-Leu-Val-Tyr-AMC (SEQ. ID. NO. 1), Z-Leu-Leu-Arg-AMC and Z-Leu-Leu-Glu-2NA, where Suc is N-succinyl, AMC is 7-aminomethylcoumarin, Z is carbobenzyloxy and 2NA is 2-naphthylamine.

Publicly accessible databases such as MIPS ("Munich information centre for protein sequences") or SGD ("saccharomyces genome database") describe all subunits of the 26S proteasome, with a few exceptions, as essential.

Various reversible and irreversible inhibitors for the enzymic activity of proteasomes in vitro are also known to exist. Thus, Klafky et al. (1995), *Neuroscience Letters* 201, 29-32 studied the action of the proteasome inhibitor calpain inhibitor 1 on the secretion of the β-amyloid peptide.

Fenteany et al. (1995), *Science*, 268, 726-731 describe lactacystin as metabolite of streptomycetes, which acts as a cell cycle inhibitor and leads to the induction of neurite growth in murine neuroblastoma cells. The cellular target for this inhibitor is the 20S proteasome.

Kroll et al. (1999) *Chem. Biol.* 6, 889-698 describe a fungal metabolite, epipolythiodioxopiperazine (gliotoxin), which suppresses, inter alia, antigen processing in mammalian cells.

As the authors were able to show, gliotoxin is a non-competitive inhibitor of the 20S proteasome in vitro.

Mellgren (1997) *J. Biol. Chem.* 272(47), 29899-29903 describes the inhibitory action of various peptidyl compounds on the human 20S proteasome. This publication further describes that the said substances at concentrations of 200 μM had no effect on the growth of fungal cells (*S. cerevisiae*). In agreement therewith, Lee and Goldberg (1998), (Proteasome inhibitors cause induction of Heat shock proteins and trehalose, which together confer thermotolerance in *Saccharomyces cerevisiae*, *Molecular and Cellular Biology* 18, 30-38) demonstrate that pharmacologically highly effective proteasome inhibitors such as MG-132 (Z-Leu-Leu-Leu-CHO) have only a minimum effect, if any, on the growth rate of yeast cells at 30° C.

Stack et al. (2000), *Nature Biotechnology* 18, 1298-1302 describe a cellular assay system for identifying inhibitors of the proteasome and indicate the possible use of these inhibitors for the treatment of Alzheimer's or Parkinson's disease. Here, the half-life of proteins is shortened by genetically modifying ubiquitin in such a way that proteins labelled therewith are destabilized. If an inhibit prevents protein degradation, it is possible to determine this on the basis of a reporter gene.

WO 00/33654 A1 describes the use of proteasome inhibitors for the treatment of various human disorders. A starting point for the action of the said inhibitors, which is mentioned here, is the immunomodulating activity of the 26S proteasome.

Thus, the proteasome has hitherto been described as a target protein for the treatment of various disorders of the human organism. Whether the proteasome from fungi is also accessible for active compounds and whether it can be inhibited or modulated by the latter, and whether such active compounds may also be used in vivo, i.e. as fungicides, has hitherto neither been studied nor described in detail. Mellgren (1997), *J. Biol. Chem.* 272(47), 29899-29903 only reveals that the inhibitors of the human proteasome described therein have, at a concentration of 200 μM, no inhibitory action on yeast cells. Lee and Goldberg (1998) furthermore demonstrate that pharmacologically highly effective proteasome inhibitors have only a minimal effect, if any, on the growth rate of yeast cells.

Thus, the prior art only reveals that, although inhibitors of the human proteasome exist, these inhibitors exhibit no action in fungi. The fungal proteasome thus seems inaccessible to the inhibitory action of the compounds. It would nonetheless be desirable to provide new fungicides which have new sites of action and mechanisms in order to prevent thereby, for example, the development of resistance to known fungicides with different sites of action and to develop more effective or more specific, and thereby also environmentally more compatible fungicides.

SUMMARY OF THE INVENTION

It was therefore the object of the present invention to provide a novel target from fungi for the identification of funigicides.

Surprisingly, it was now found within the scope of the present invention that, despite the findings of Mellgren (1997) and Lee and Goldberg (1998), the fungal 26S or 20S proteasome which hitherto has been known as being unsuitable in connection with the development of new fungicides is an effective target protein for specific inhibitors. Furthermore, it was found that such inhibitors can be identified in suitable methods and that the inhibitors found by the said methods, surprisingly, can also be used as fungicides. It was also found that already known inhibitors of the human or animal proteasome can also be used as fungicides or for preparing a medicament for the treatment of fungal infection in humans or animals.

Thus, it was found within the scope of the present invention that active compounds can inhibit fungal 26S or 20S proteasomes in vitro and that the treatment with these active compounds can damage and destroy a fungal organism treated with these active compounds. The inhibitors of fungal 26S/20S proteasomes can thus be used as antimycotics and, in particular, also as fungicides in plant protection. The present invention shows, for example, that inhibiting *S. cerevisiae* 20S proteasomes (Example 1) is as successful as inhibiting *U. maydis* and *B. cinerea*, both of which are plant-pathogenic fungi, 20S proteasomes (Example 2). The treatment of these fungi with the substances identified in assay methods according to the invention and with known proteasome inhibitors results in the death of the fungi in synthetic media and on the plant.

The present invention therefore relates to the use of 26S and/or 20S proteasomes, preferably fungal 20S proteasomes, for identifying fungicides.

BRIEF DESCRIPTION OF THE DRAWINGS

In FIG. 5A, half the amount of protein was used compared to FIG. 5B. 5% DMSO is particularly suitable for the reaction.

DETAILED DESCRIPTION OF THE INVENTION

Definitions

Figure 1:
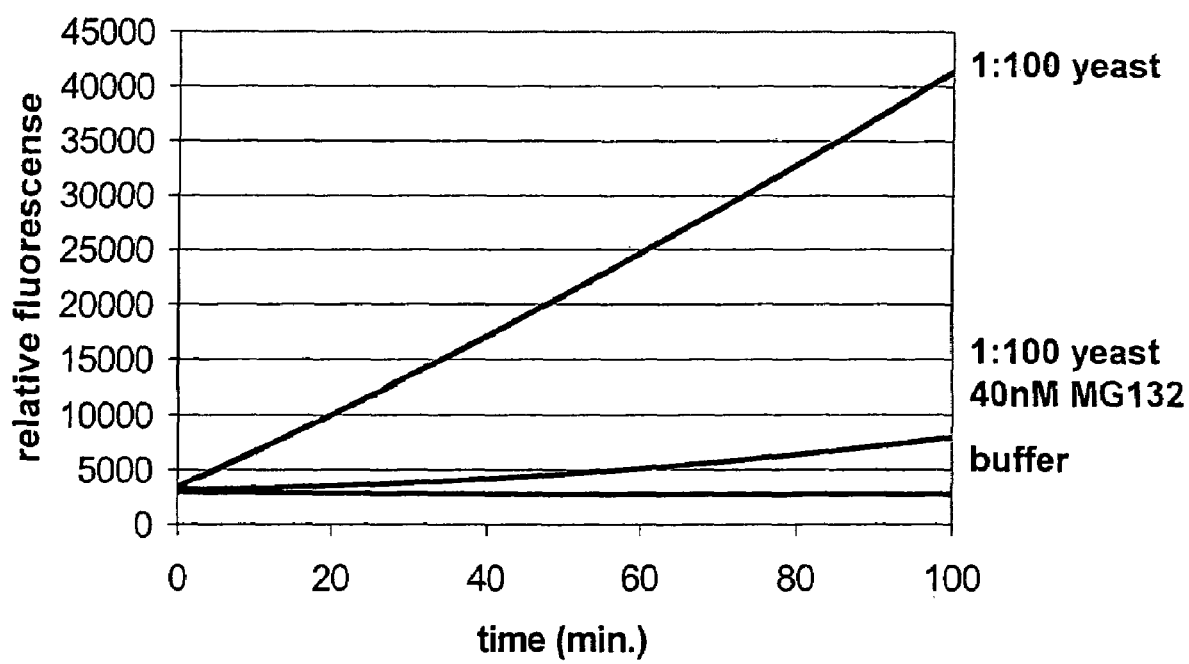
FIG. 1 is an activity assay for the 20S proteasome from yeast. The substrate used for the chymotryptic activity was Suc-LLVY-AMC (SEQ. ID. NO. 1). Liberation of AMC was determined fluorometrically as a function of time. The proteasome activity was determined in a 1:100 dilution of a yeast extract in the presence of 40 nM MG132 and in the absence of MG-132. As a negative control, the reaction was carried out without enzyme (buffer).

The term "fungicide(s)", as used hereinbelow, comprises both substances used in crop protection which are used for controlling plant-pathogenic fungi and substances which are used for controlling human- or animal-pathogenic fungi (antimycotics).

"Inhibitors" may be small organochemical molecules, peptides or antibodies which bind to or influence the activity of the 20S or the larger 26S polypeptide complexes. Furthermore, inhibitors may be small organochemical molecules, peptides or antibodies which bind to a molecule which in turn binds to the polypeptides of the invention and thereby influences the biological activity thereof. Inhibitors may be natural substrates and ligands or structural or functional mimetics thereof. Preferably, however, the term "inhibitor", as used herein, comprises those molecules which do not constitute the natural substrates or ligands. The term "inhibitors of the 26S and/or 20S proteasome", as used herein, refers to inhibitors which are capable of specifically inhibiting one or more enzymic activities of the proteasome.

Discussion

It is possible to use 20S proteasomes from various fungal species such as those listed below, for example, for identifying fungicides. Thus it is possible, for example, to use *S. cerevisiae* 20S proteasomes in an inventive assay method for identifying fungicides (Example 1, FIG. 1) as well as 20S proteasomes from the plant-pathogenic fungi *U. maydis* (Example 2, FIG. 2) and *B. cinerea* (FIG. 3).

The compounds identified with the aid of methods suitable for identifying inhibitors of the 26S/20S proteasome act on a large variety of fungi such as, for example, human-pathogenic fungi or plant-pathogenic fungi. These include, for example, the following fungi from the range of plant-damaging fungi, with the list not being exhaustive, however:

Plasmodiophoromycetes, oomycetes, chytridiomycetes, zygomycetes, ascomycetes, basidiomycetes and deuteromycetes, for example

*Pythium* species such as, for example, *Pythium ultimum, Phytophthora* species, such as, for example, *Phytophthora infestans, Pseudoperonospora* species, such as, for example, *Pseudoperonospora humuli* or *Pseudoperonospora cubensis, Plasmopara* species, such as, for example, *Plasmopara viticola, Bremia* species, such as, for example, *Bremia lactucae, Peronospora* species, such as, for example, *Peronospora pisi* or *P. brassicae, Erysiphe* species, such as, for example, *Erysiphe graminis, Sphaerotheca* species, such as, for example, *Sphaerotheca fuliginea, Podosphaera* species, such as, for example, *Podosphaera leucotricha, Venturia* species, such as, for example, *Venturia inaequalis, Pyrenophora* species, such as, for example, *Pyrenophora teres* or *P. graminea* (conidial form: Drechslera, syn: Helminthosporium), *Cochliobolus* species, such as, for example, *Cochliobolus sativus* (conidial form: Drechslera, syn: Helminthosporium), *Uromyces* species, such as, for example, *Uromyces appendiculatus, Puccinia* species, such as, for example, *Puccinia recondita, Sclerotinia* species, such as, for example, *Sclerotinia sclerotiorum, Tilletia* species, such as, for example, *Tilletia caries; Ustilago* species, such as, for example, *Ustilago nuda* or *Ustilago avenae, Pellicularia* species, such as, for example, *Pellicularia sasakii, Pyricularia* species, such as, for example, *Pyricularia oryzae, Fusarium* species, such as, for example, *Fusarium culmorum, Botrytis* species, *Septoria* species, such as, for example, *Septoria nodorum, Leptosphaeria* species, such as, for example, *Leptosphaeria nodorum, Cercospora* species, such as, for example, *Cercospora canescens, Alternaria* species, such as, for example, *Alternaria brassicae* or *Pseudocercosporella* species, such as, for example, *Pseudocercosporella herpotrichoides.*

Others which are of particular interest are, for example, *B. cinerea, Magnaporthe grisea, Cochliobulus heterostrophus, Nectria hematococcus* and *Phytophthora* species, plasmodiophoromycetes, oomycetes, chytridiomycetes, zygomycetes, ascomycetes, basidiomycetes and deuteromycetes.

The inhibitors of the fungal 20S proteasome may also be used on the human- or animal-pathogenic fungi which are mentioned below by way of example but not exhaustively:

Dermatophytes such as, for example, *Trichophyton* spec., *Microsporum* spec., *Epidermophyton floccosum* or *Keratomyces ajelloi*, which cause, for example, Athlete's foot (Tinea pedis), Yeasts such as, for example, *Candida albicans*, which causes candidal oesophagitis and dermatitis, *Candida glabrata, Candida krusei* or *Cryptococcus neoformans*, which can cause, for example, pulmonary cryptococcosis and also torulosis, Moulds such as, for example, *Aspergillus fumigatus, A. flavus, A. niger*, which cause, for example, bronchopulmonary aspergillosis or fungal sepsis, *Mucor* spec., *Absidia* spec., or *Rhizopus* spec., which cause, for example, zygomycoses (intravasal mycoses), *Rhinosporidium seeberi*, which causes, for example, chronic granulomatous pharyngitis and tracheitis, *Madurella myzetomatis*, which causes, for example, subcutaneous myzetomas, *Histoplasma capsulatum*, which causes, for example, reticuloendothelial cytomycosis and Darling's disease, *Coccidioides immitis*, which causes, for example, pulmonary coccidioidomycosis and sepsis, *Paracoccidioides brasiliensis*, which causes, for example, South American blastomycosis, *Blastomyces dermatitidis*, which causes, for example, Gilchrist's disease and North American blastomycosis, *Loboa loboi*, which causes, for example, Keloid blastomycosis and Lobo's disease, and

*Sporothrix schenckii*, which causes, for example, sporotrichosis (granulomatous dermal mycosis).

Fungicidally active compounds which are found with the aid of the fungal 20S proteasome from, for example, *S. cerevisiae* or *U. maydis* may thus also interact with numerous other fungal species, the interaction with the different 26S or 20S proteasomes present in these fungi not necessarily always being equally strong. This explains, inter alia, the observed selectivity of the substances acting on this polypeptide complex.

A number of activity assays for the proteasome are already known and partially also commerically available (e.g. "20S Proteasome Assay Kit, SDS-Activated" from Calbiochem) which may be used for testing the activity of the proteasome in small amounts and in a relatively time-consuming manner, i.e. using several pipetting steps. These known activity assays may be utilized, for example, in order to identify the fungicides of the invention. An HTS-capable method, however, which allows the identification of inhibitors of the 26S and/or the 20S proteasome is not known as yet. Known methods which, on a small scale, may be used for assaying individual compounds or the inhibitory action thereof are, due to their complexity, unsuitable for testing in an HTS or UHTS system whole substance libraries systematically and with sufficient reliability. However, compared to other methods, these systems are particularly attractive, since a very large number of potential inhibitors can be tested in a short time and with good reproducibility.

This is particularly interesting for the 20S proteasome, since here a plurality of enzymic activities whose inhibition by a potential inhibitor can also be observed in each case specifically are combined in one enzyme. The time needed therefor can be markedly reduced by utilizing an HTS or UHTS system and the probability of identifying an inhibitor with desirable properties can be markedly increased. These different enzymic activities can be analysed and separated from one another on the basis of substrates specific for these individual activities (McCormack et al. (1998), *Biochemistry* 37, 7792-7800), and this is particularly important in order to influence the specificity and action of the inhibitors and thus to find also inhibitors or fungicides which are damaging to fungi or to particular fungal genera or species but not to other organisms such as, for example, plants, insects or mammals. Various specific inhibitors are already known in humans (human proteasome). However, there are also inhibitors which influence a plurality of proteasome activities.

It was also therefore the object of the present invention to provide an in-vitro method accessible to HTS and UHTS methods, which makes possible the identification of, where appropriate, specific inhibitors of the proteasome on a large scale and which allows, where appropriate, subsequent classification into particular enzymic activities of the polypeptide complex. Inhibition of suitable proteolytic activities can thus reduce, for example, the toxicity for higher eukaryotes. In addition, the individual biological activities can be separated and specifically modulated accordingly. This is important in medicine in order to reduce, for example, cytotoxic effects by not inhibiting those activities which are not targets of the therapy.

We have now found a method which makes it possible, on the basis of HTS-capable in-vitro assays, to filter inhibitors of the fungal proteasome out of a multiplicity of compounds to be assayed, the "candidate compounds", and to relate them, where appropriate, to a specific proteolytic activity of the 20S proteasome.

In this connection, the method of the invention is based on two improvements of the overall method. Firstly, the present invention enables an efficient but, at the same time, considerably faster and simpler preparation of proteasome extracts, and, secondly, the stability of the assay components was increased, as a result of which the steps required for carrying out an activity assay were also reduced. The rapid and efficient proteasome purification is based on introducing an incubation step at elevated temperature, which is described in more detail below. The increase in the stability of the reaction components, with attainment of an excellent signal-to-background ratio and simultaneous reduction of the steps required in the activity assay, was surprisingly made possible by increasing the concentration of the DMSO to unusually high values. An optimal required DMSO concentration was determined.

The abovementioned method for preparing an active 20S proteasome extract has not been described previously. The mentioned HTS-capable methods for identifying inhibitors of 26S/20S proteasomes, in particular of fungal proteasomes, have likewise not been described previously.

The present invention therefore also relates to a method for isolating/purifying 20S proteasomes from eukaryotic cells, in particular of 20S proteasomes from fungal cells, the method being suitable in particular for yeast cells or cells of *U. maydis* or *B. cinerea*.

The present invention furthermore relates to an HTS-/UHTS-capable method for identifying inhibitors of the 26S/20S proteasome, such as, for example, the 26S/20S proteasome of mammals, in particular humans, and in particular of the fungal 26S/20S proteasome, by using a specifically adapted inhibition assay. Particular preference is given to using the method for identifying inhibitors of the fungal 26S/20S proteasome and for identifying fungicides.

In addition to inhibiting the proteasome in vitro, it is crucial, in order to be able to use the inhibitors in question also as fungicides, that the identified compounds are also active in vivo, i.e. can indeed be used as fungicides, for example in agriculture. Many inhibitors found in in-vitro assays are, for various reasons, not capable of damaging the target organism itself. Thus, as described above, no action of known inhibitors of the human proteasome in fungi has been found in the prior art.

It was therefore also the object of the present invention to make accessible the use of inhibitors of the fungal 20S proteasome as fungicides.

It is demonstrated within the scope of the present invention that the proteasome inhibitors identified, for example, on the basis of the method of the invention described below, but also already known inhibitors of, for example, the human proteasome, are, contrary to expectation, effective fungicides, i.e. substances which not only exhibit an inhibitory action in vitro but can also be used in vivo in order to interfere with the function of the fungal proteasome and to damage or destroy the fungus in question.

It is, in this connection, not necessary to use the method of the invention described below in order to identify the inhibitors of the fungal 20S proteasome. Rather it is possible to use all known methods for determining the activity of the 20S proteasome, as long as they permit evaluation of the inhibitory action of a candidate compound on the fungal 20S proteasome.

The present invention therefore also relates to a method for identifying fungicides by contacting 20S proteasomes, preferably fungal 20S proteasomes, with a candidate compound and subsequently selecting the compound(s) inhibiting the enzymic activity of the 20S proteasome. Preference is given to carrying out the method in such a way that the enzymic activity of the 20S proteasome is measured in the presence and absence of a candicate molecule, selecting those candidate compounds which reduce the enzymic activity of the proteasome compared to the control in the absence of a candidate compound, i.e. which are proteasome inhibitors.

The term "proteasome inhibitor" as used herein refers to a substance which inhibits directly or indirectly at least one, or else, where appropriate, a plurality of the abovementioned enzymic activities. Such an inhibitor is preferably specific, i.e. it inhibits proteasome activity at a concentration which is lower than the concentration of an inhibitor which is required in order to cause a different effect not associated therewith. Preferably, the concentration is twice as low, in particular preferably five times as low and very particularly preferably at least ten times or 20 times as low, as the concentration of a compound required for causing an unspecific effect.

The term "proteasome activity" as used herein refers to one or more of the abovementioned enzymic activities of the 20S or 26S proteasome.

Within the scope of the present invention, in each case 20S proteasomes from S. cerevisiae, U. maydis and B. cinerea were used, by way of example, in order to identify inhibitors of the 26S and/or 20S proteasome. However, it is also possible to use, instead of the 20S proteasome from S. cerevisiae, U. maydis or B. cinerea, 20S proteasomes from other fungi or from other, non-fungal organisms to identify inhibitors. This is made clear by the fact that inhibitors of the human proteasome can also act as fungicides.

The cells can be disrupted by means of various techniques known to the skilled worker. Likewise, subsequent purification/isolation of the proteasomes can also be achieved using known methods (e.g. Groll et al. (1997), Structure of the 20S proteasome from yeast at 2.4 Å resolution, *Nature* 386, 463-471; EP 345 750 A2; WO 98/42829; JP 05292964 A; JP 06022759 A). The terms "isolation", "concentration" or "purification", as used herein, mean that the 20S proteasomes are removed from other proteins or other macromolecules of the cell or of the tissue to such an extent that a specific measurement of their enzymic activity or inhibition thereof can take place. Preferably, a composition containing the 20S proteasomes is, with respect to the proteasome content, at least 10 times, and particularly preferably at least 100 times, concentrated, in comparison with a preparation from the host cells. The known methods are relatively complex and comprise a number of steps (cf. e.g. WO 98/42829). It is desirable, in particular for the use of proteasomes in methods of the invention, to recover, in a short time, 20S proteasomes which are at least as active as the 20S proteasomes prepared by complicated methods of the prior art and which permit measurement of their enzymic activity and inhibition thereof.

In the present method of the invention, the yeast cells are disrupted using methods known to the skilled worker, preferably mechanically (e.g. by using a French Press or a high-pressure homogenizer) in the assay buffer used later (e.g. 50 mM Tris-HCl, pH 7.5, 10 mM EDTA). Examples of yeasts suitable for the method of the invention include also commercially available yeasts (baker's yeast) as used for baking. The proteasomes are then in the soluble fraction and can be separated from insoluble components and cell debris by centrifugation, although this step need not necessarily be carried out in the method of the invention. The suspension or soluble fraction is then incubated at from approx. 50° C. to 70° C., preferably from 55° C. to 65° C., for approx. 20 to 75 minutes. An incubation at approx. 60° C. for approximately 60 minutes is particularly suitable. The finding that the protein is stable at this temperature, in contrast to the other proteins still present, is utilized here. Therefore, temperature-labile proteins precipitate in this purification step of the invention and can be removed by centrifugation from the temperature-stable 20S complex. Accordingly, the incubation can be stopped when cell components are no longer denatured and precipitate. The use of a heating step for separating the proteasome from other cell components is not described in the prior art. However, it makes possible a rapid, simple and very efficient purification of proteasomes in just one step, and the proteasomes purified in this way can be used, after removing the precipitated cell components, directly in activity or inhibition assays. Subsequently, for example, sodium azide may be added to the supernatant in order to prevent microbial growth. Moreover, the method of the invention ensures that preferably 20S proteasomes are obtained and not 26S proteasomes which are more unsuitable for identifying inhibitors, because proteolytically active regions in complete 26S proteasomes may not be accessible. It is possible, in this simple manner, to obtain from 30 g of yeast (wet weight) sufficient proteasomes for use in an HTS-capable method for identifying inhibitors.

The present invention therefore relates to a method for purifying 20S proteasomes from eukaryotic cells, preferably fungal 20S proteasomes, which is characterized in that
a) cells, preferably fungal cells, are disrupted using common methods,
b) the cell suspension generated is heated to from 50° C. to 70° C., until the temperature-sensitive components have precipitated, an
c) the proteasomes are recovered by removing the insoluble components by means of centrifugation.

The method for purifying 20S proteasomes can be used in various organisms. Thus it is demonstrated within the scope of the present invention that it is possible to obtain from, for example, S. cerevisiae, U. maydis and B. cinerea 20S proteasomes with high activity with the aid of the method of the invention. Analogously, the method may also be utilized for other eukaryotic, in particular for fungal cells.

Methods for assaying the enzymic activity of 20S proteasomes and for assaying the inhibition of this activity are known from the literature. These assay systems utilize, for example, particular proteasome substrates whose enzymic degradation results in the liberation of a fluorometrically or colorimetrically determinable group. The methods used are based on the step-wise addition of the individual components (e.g. reaction buffer, activation buffer, 20S proteasomes, substrate solution, inhibitor) and a subsequent measurement of the changing fluorescence or absorption (see, for example, "20S Proteasome Assay Kit, SDS-Activated from Calbiochem" Cat. No. 539158). In this connection, it must be taken into account that the stability of the substrate is low under experimental conditions. The peptide substrates such as, for example, Suc-LLVY-AMC (SEQ. ID. NO. 1) are relatively unstable, due to their low solubility and stability, and therefore hardly suitable for measurements lasting several hours, as is unavoidable, for example, in HTS-/UHTS-systems when measuring an extremely large number of samples which need to be introduced and measured. The substrates or the activity assays based thereon have therefore been suitable hitherto only for short-term single experiments which ensure that the peptide substrate used is still intact. Thus, the substrate Suc-LLVY-AMC (SEQ. ID. NO. 1) is described as being slightly soluble (50 mg/ml in DMSO) and light-sensitive. A typical experimental approach ("20S Proteasome Assay Kit, SDS-Activated" from Calbiochem) is based on carrying out the following fundamental steps: first, a reaction buffer is introduced, activation buffer (containing SDS, for example) is added by pipetting in a second step, and both components are mixed. In a third step, 20S proteasomes are added to this solution. In a fourth step, the substrate is added, thereby starting the reaction. In a fifth step, the inhibitor is added, and it is possible to carry out the last two steps optionally also in reverse order.

In order to render an activity assay of this type usable for HTS-/UHTS-methods, the large number of pipetting steps would have to be reduced. For this, the mixtures of the in this case individually pipetted components in turn would have to remain stable over a relatively long period, in order to take into account the usually long time required for preparing the samples and measuring numerous candidate compounds. In this connection, the enzymic activity of the proteasome as well as that of the substrate should not be impaired in order to maintain the required signal-to-background ratio. It was therefore the object of the present invention to further develop the known assay systems so as to make possible the use thereof in HTS-/UHTS-methods.

Figure 5:
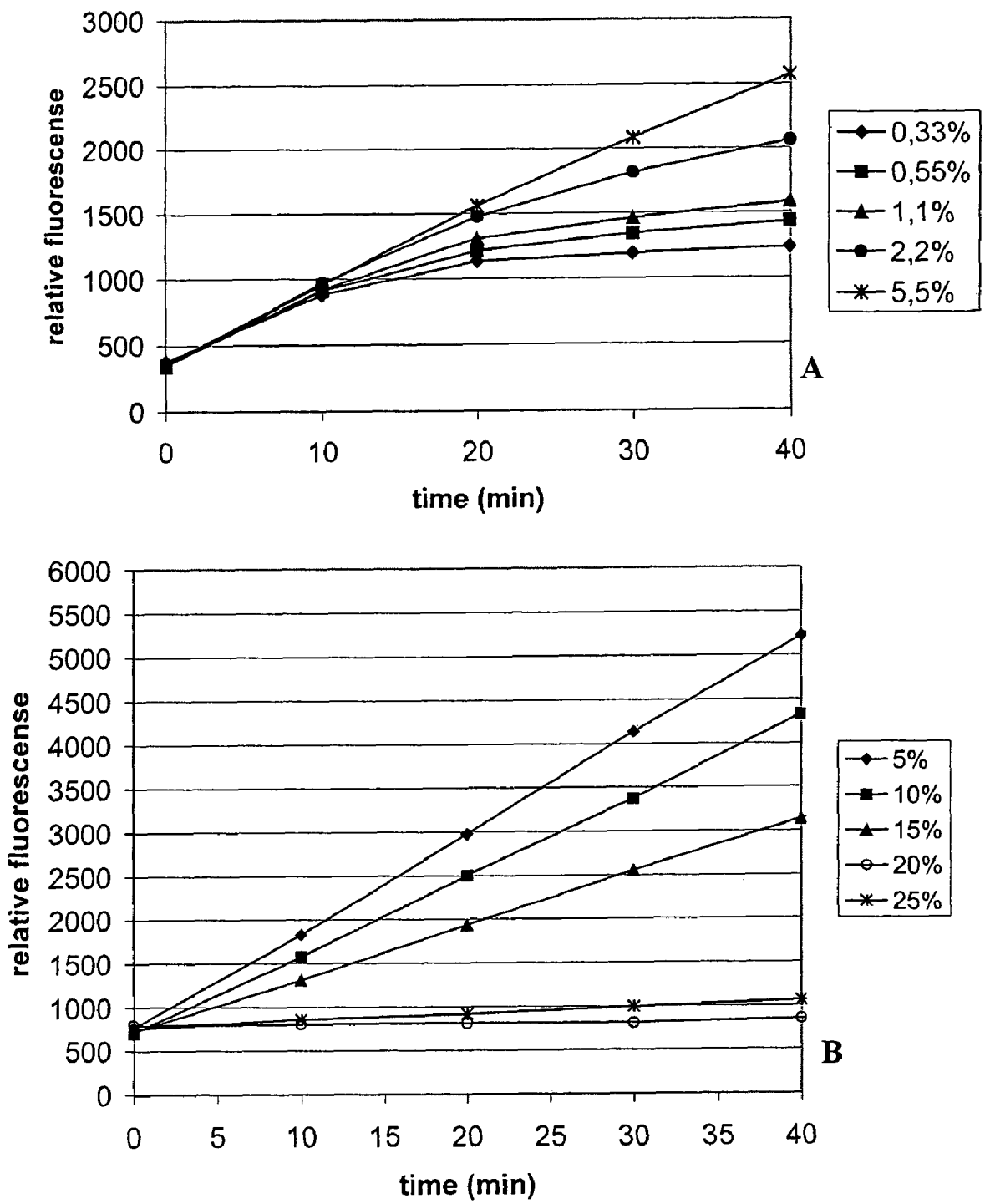
FIGS. 5A and 5B illustrate the dependence of the reaction on the amount of dimethyl sulphoxide ("DMSO") used. The activity of the 20S proteasome from yeast was determined on the basis of AMC liberation as a function of time. Increasing amounts of DMSO were added to the reaction as illustrated in FIGS. 5A and 5B.
Figure 6:
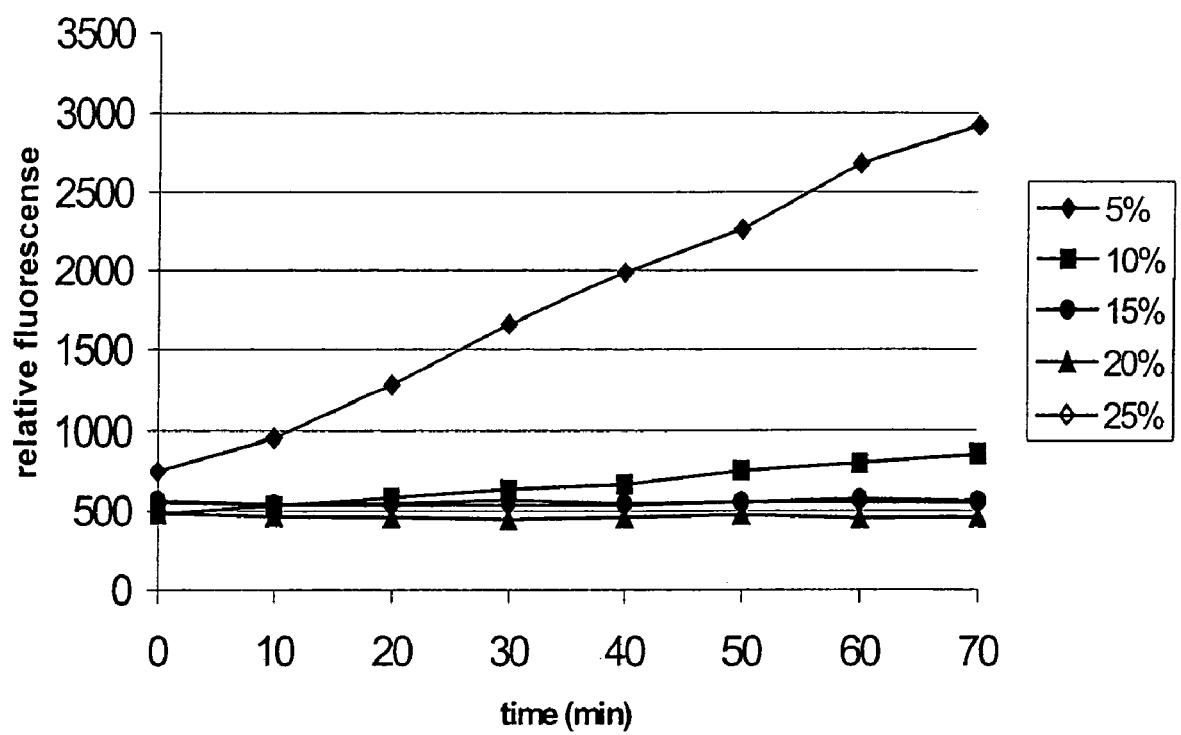
FIG. 6 illustrates the effect of storage and stability of the reaction components and their dependence of the reaction on the amount of DMSO used. The dependence of the reaction on the amount of DMSO used was determined in FIG. 6 in the same fashion as described in FIGS. 5A and 5B. However, the components of the reaction in FIG. 5(B) were stored at 4° C. for 72 hours before their use in FIG. 6. In the presence of 5% DMSO, the reaction is stable even after 72 hours. Higher quantities of DMSO lead to the loss of activity.
Figure 7:
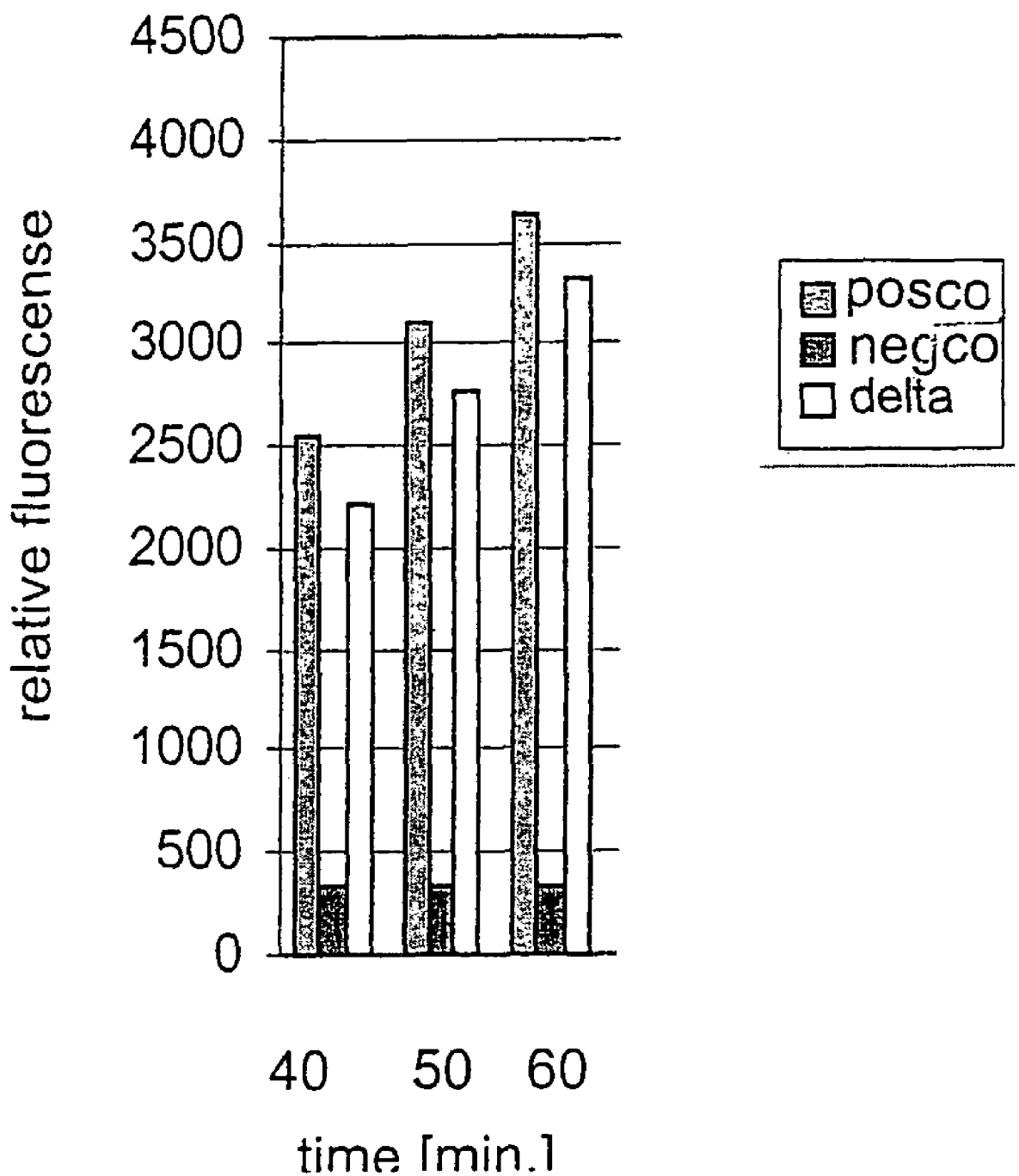
FIG. 7 illustrates the detection of the activity of the 20S proteasome in a 384-well microtitre plate ("MTP"). AMC fluorescence was determined in in each case 192 wells after 40, 50 and 60 minutes. "Posco" corresponds to the reaction with enzyme, "negco" corresponds to the reaction without enzyme, "delta" is the different between the two values. Even after 40 min, a z factor of >0.7 was attained. The z factor is a mathematical parameter for calculating the uniformity of the recorded data and thus allows an evaluation of the usability of an assay for a screening of substances. The z factor is calculated as follows: z factor=1−((3×standard deviation posco+ 3×standard deviation negco)/(average posco−average negco)), (Zhang et al. (1999), A Simple Statistical Parameter for Use in Evaluation and Validation of High Throughput Screening Assays. *J. Biomol. Screen.* 4(2), 67-73).

The solution of the problem is based on using DMSO (dimethyl sulphoxide) in the reaction mixture or on increasing the concentration of DMSO in the reaction mixture. It was found that, for example, the chymotryptic activity of the proteasome decreases with increasing DMSO concentrations (FIG. 5(B)), while stability of the substrate increases with increasing DMSO concentrations. Finally, maintaining optimal chymotryptic activity, optimal substrate stability was obtained at a concentration of from 2 to 10% DMSO (v/v), with a concentration of from 3 to 7% being particularly desirable. A DMSO concentration of from 4.5 to 6% (FIGS. 5(A) and (B)) is particularly suitable. At a concentration of 5% DMSO, the proteasome activity remains stable even for 72 h, and not just for approx. 1 h as described in the prior art (FIG. 6).

As a result, the method of the invention markedly increases the stability of the substrate, without impairing the activity of the proteasome. In addition to a distinctly increased period which can be utilized for carrying out the activity or inhibition assays, it is also possible, according to the present invention, to combine the required solutions already beforehand and store them over a relatively long period (FIG. 6) and thereby to reduce the number of the pipetting steps required to three pipetting steps instead of up to five steps in the known methods (see above). For example, the candidate compound is initially introduced in a suitable buffer and, in a second step, the substrate solution containing a suitable amount of DMSO and possibly also already the activator SDS is added. In a third step, the 20S proteasome solution is added, thereby starting the reaction. The order of addition of the individual components may also be varied.

The temperatures used in the method of the invention may be varied over a very wide range. It is possible to use temperatures of from 15° C. to 80° C., in particular from 25° C. to 50° C., or simply room temperature. Particular preference is given to using a temperature of 37° C.

It is also possible to use in the method of the invention activators of the 20S proteasome which are contained in the reaction mixture. Preferred activators are the activators described in Coux et al. (1995), *Ann. Rev. Biochem.* 65, 801-847, with particular emphasis on the activators SDS (sodium dodecyl sulphate) and PA28α (Knowlton et al. (1997), *Nature* 390, 639-643).

The present invention therefore also relates to a method for identifying inhibitors of 20S proteasomes, in particular of fungal 20S proteasomes, by assaying a candidate compound in a 20S proteasome-inhibition assay in the presence of from 2 to 10% DMSO (v/v). Inhibition of the enzymic activity of the 20S proteasome by the candidate compound may be monitored by comparing fluorescence or absorption in the presence and absence of the candidate compound.

The present invention also relates to a method for identifying fungicides, as described above and below, which may be followed by an in-vivo assay for determining the fungicidal activity. This assay preferably comprises contacting the inhibitor found with at least one fungal species and subsequently testing the damage to the fungus.

In this connection, the term "20S proteasome-inhibition assay" as used herein refers in particular to measuring the enzymic activity of 20S proteasomes on the basis of the fluorescence or absorption resulting from the liberation of a fluorogenic or colorimetrically determinable group from a substrate of the 20S proteasome, or of the inhibition of this liberation by an inhibitor of the activity in question. The method of the invention should be applied, in particular, if the inhibition assay is based on the use of a labile substrate which can be stabilized by DMSO.

In the natural context, the 20S proteasome hydrolyses unprotected peptides so that it is also possible to use unprotected substrates in the method of the invention. However, the possibility of a further reduction in stability compared to protected substrates should be taken into account. In addition to the fluorophore AMC, other fluorophores or else chromophores may also be used, such as, for example, the fluorophores 2-naphthylamide (2NA), 4-methoxy-2-naphthylamide or 6-amino-quinoline. Examples of colorimetrically determinable groups are p-nitroanilide (pNA), p-phenylazoanilide or 3,5-dibromo-4-hydroxyanilide. Known substrates for the various ezymic activities of the proteasome are, inter alia, the below-mentioned peptide substrates whose degradation can be monitored fluorimetrically or colorimetrically. Examples of such substrates are Z-Leu-Leu-Leu-AMC (Z-LLL-AMC) for measuring chymotryptic activity, Z-Leu-Leu-Glu-AMC (Z-LLE-AMC) for measuring the peptidyl-glutamyl peptide-hydrolysing activity, Z-Val-Lys-Met-AMC (Z-VKM-AMC) for measuring the chymotryptic activity, Suc-Leu-Tyr-AMC (Suc-LY-AMC) for measuring the chymotryptic activity, Z-Leu-Leu-Glu-2NA (N—(N-carbobenzyloxycarbonyl-leucyl-leucyl-arginyl)-2-naphthylamine) or Suc-Leu-Leu-Val-Tyr-AMC (Suc-LLVY-AMC) (SEQ. ID. NO. 1) for measuring the PGPH or the chymotrypsin-like activity, all of which are commercially available (see also WO 00/23614). Substrates which may be used are also the above-mentioned substrates, in particular Suc-LLVY-AMC (SEQ. ID. NO. 1), carrying different protective groups. Examples of frequently used protective groups are benzyloxycarbonyl (also referred to as "Z", see above) and N-tert-butoxycarbonyl (t-boc).

The present invention therefore relates in particular to methods in which at least one substrate selected from the abovementioned group of substrates is used, with preference being given to using a substrate selected from the following group of substrates: Z-LLL-AMC, Z-LLE-AMC, Z-VKM-AMC, Suc-LY-AMC, and in particular Suc-LLVY-AMC (SEQ. ID. NO. 1).

In addition, covalent and competitive inhibitors are known, such as, for example, clasto-lactacystin β-lactone, epoxomicin (inhibits the chymotrypsin-like, trypsin-like and peptidyl-glutamyl peptide-hydrolysing activity of the proteasome), Z-Leu-Leu-Leu-B(OH)$_2$, Z-Leu-Leu-Leu-CHO (MG-132, inhibits degradation via the ubiquitin pathway), Z-Leu-Leu-Nva-CHO (MG-115, carbobenzoxy-L-leucyl-L-leucyl-L-norvalinal, specifically inhibits the chymotrypsin-like activity of the proteasome), Z-lleu-Glu(OtBu)Ala-Leu-CHO (SEQ. ID. NO. 2), Z-Leu-Leu-Phe-CHO (inhibits the chymotrypsin-like activity), Ac-Leu-Leu-Nle-CHO (MG-101, Ac-Leu-Leu-norleucinal, inhibits the chymotrypsin-like and the peptidase activity) or Ac-Leu-Leu-Met-CHO (inhibits the peptidase activity), all of which are likewise commercially available (see also Mellgren (1997): Specificities of Cell Permeant Peptidyl Inhibitors for Proteinase Activities of μ-Calpain and the 20S Proteasome. *J. Biol. Chem.* 272, 29899-29903; Bogyo et al. (1998): Substrate binding and sequence preference of the proteasome revealed by active-site-directed affinity probes. *Chem. Biol.* 5, 307-320). These known inhibitors may thus also be used for checking the method of the invention (see Example 3). In further assays on fungal cells it was found that these known inhibitors surprisingly also have a fungicidal action and can therefore also be used as fungicides or for preparing a medicament for treating fungal infection.

The particular enzymic activity or else a plurality of activities of the proteasome may be measured fluorimetrically or colorimetrically in principle on the basis of the abovementioned known substrates or cleavage products thereof, and inhibition of this activity may be tested with the aid of any of the abovementioned known inhibitors. For this purpose, it is possible to choose, depending on the target activity, the corresponding substrates and, where appropriate, inhibitors. The inhibitors found using a method of the invention or a specific substrate may then be identified directly as inhibitors of one or more specific activities.

However, the choice of the substrate must make it possible to evaluate the measurement results, i.e. an inhibition must be clearly detectable. An example of a statistical parameter which may be used is the signal-to-background ratio. A suitable parameter for determining the quality of a screening method or of an inhibition assay is also the z factor. Calculation of the z factor includes, in addition to the difference between signal and background, also the scattering of all data. The z factor is calculated as follows: z factor=1−((3×standard deviation posco+3×standard deviation negco)/(average posco−average negco)), where "posco" is the positive control and "negco" is the negative control (Zhang et al. (1999): A Simple Statistical Parameter for Use in Evaluation and Validation of High Throughput Screening Assays. *J. Biomol. Screen.* 4(2):67-73).

A z factor of greater than 0.7 is regarded as excellent, a z factor of from 0.15 to 0.7 as good, a z factor of from 0 to 0.15 as still adequate and a z factor of less than 0 as no longer evaluable.

The z factor in the method of the invention is above 0.7 after approx. 30 minutes.

The present invention therefore also relates to a method for identifying inhibitors of the 26S and 20S proteasomes which has a z factor of preferably greater than 0.7. A possible embodiment of a method of the invention is shown, by way of example, below, using a known inhibitor, MG-132, in order to demonstrate the principle of the method.

The enzymic proteasome activity to be tested or the inhibition thereof may be detected, as in the present example, via the increase in fluorescence of AMC liberated from the known peptide substrate Suc-LLVY-AMC (SEQ. ID. NO. 1) (Suc-Leu-Leu-Val-Tyr-AMC; Stein et al. (1996) *Biochemistry* 35, 3899) as depicted in the scheme below:

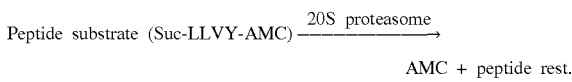

Peptide substrate (Suc-LLVY-AMC) $\xrightarrow{\text{20S proteasome}}$ AMC + peptide rest.

Suc-LLVY-AMC (SEQ. ID. NO. 1) is a fluorogenic substrate for measuring the chymotrypsin-like activity of the 20S proteasome. The AMC (7-amino-4-methoxycoumarine) removed by cleaving has an excitation maximum at a wavelength of 380 nm and an emission maximum at 460 nm. The inhibitor has a $K_i$ of 5 nM.

In principle, however, it is also possible to use, in addition to the substrate Suc-LLVY-AMC (SEQ. ID. NO. 1) mentioned here by way of example, other substrates of the proteasome, for example the known substrates indicated above.

Figure 2:
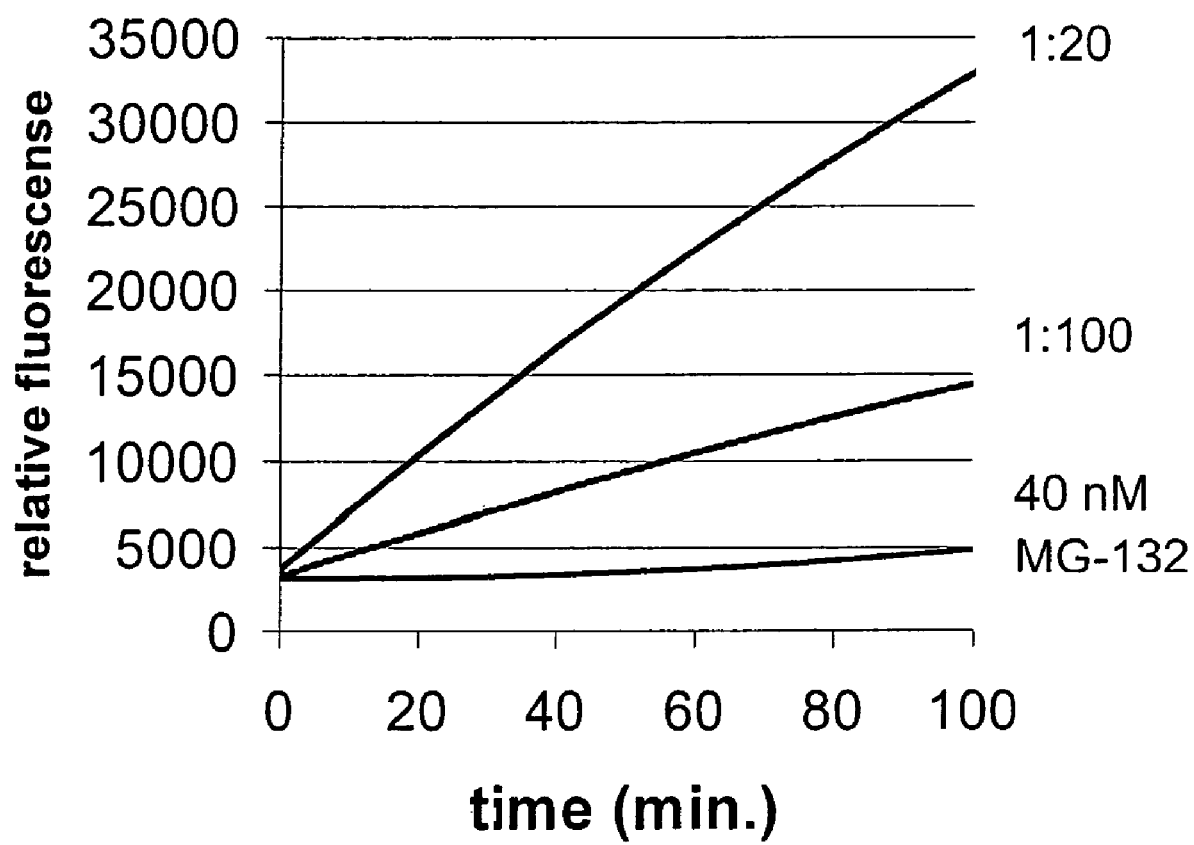
FIG. 2 is an activity assay for the 20S proteasome from *Ustilago maydis*. The substrate used for the chymotryptic activity was Suc-LLVY-AMC (SEQ. ID. NO. 1). Liberation of AMC was determined fluorometrically as a function of time. The proteasome activity was determined in a 1:100 and 1:20 dilution of a *U. maydis* preparation. Moreover, the proteasome inhibitor MG-132 was added at a concentration of 40 nM to the highest proteasome concentration.
Figure 3:
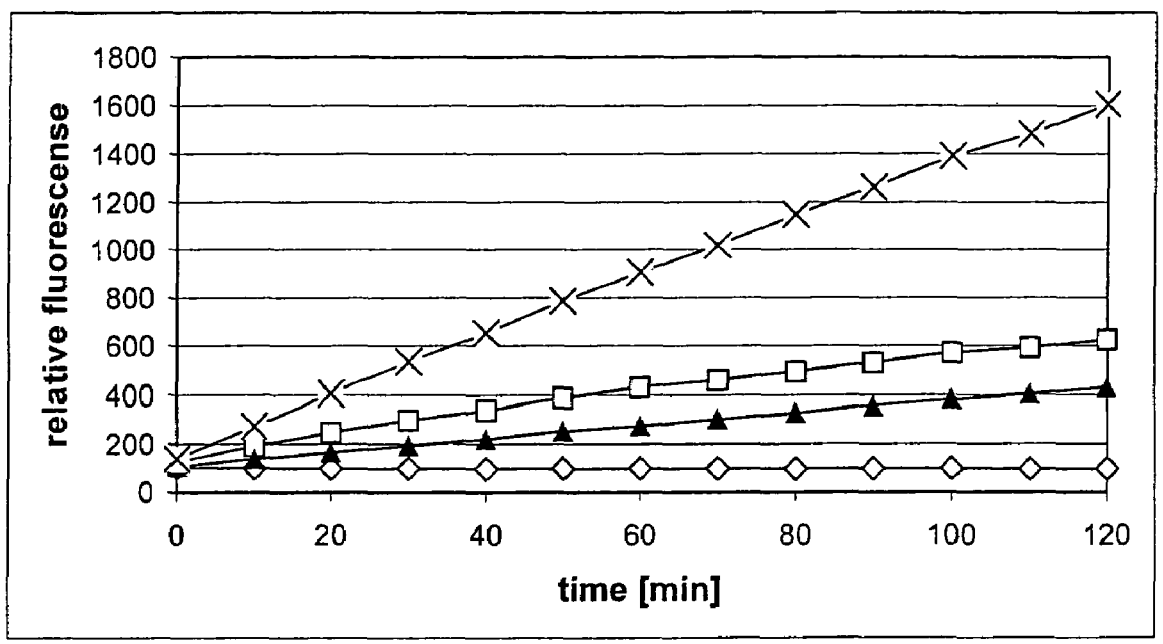
FIG. 3 is an activity assay for the 20S proteasome from *Botrytis cinerea*. The 20S proteasome from *B. cinerea* (B.c. proteasome) was isolated by preparing protoplasts from the fungal cells. The protoplasts were processed further according to the protocol for isolating the 20S proteasome from *U. maydis* (cf. Example 2). The chymotryptic activity of the B.c. proteasome was determined on the basis of the conversion of Suc-LLVY-AMC (SEQ. ID. NO. 1) (cf. Example 3). (x)=20S proteasome from *B. cinerea*, 1:100 diluted (□)=20S proteasome from *S. cerevisiae*, 1:100 diluted. (▲)=20S proteasome from *B. cinerea*, 1:500 diluted. (◇)=reaction without proteasomes.

The proteolytic activity measurable in this way can be influenced by an inhibitor such as, for example, MG-132, resulting in a lower relative fluorescence being observed (FIGS. 1 and 2). MG-132 is a known, reversible proteasome inhibitor which can penentrate cell walls (Lee, D. H., Goldberg, A. (1989) *J. Biol. Chem.* 271, 27280). Inhibition of the proteasome activity by the said known inhibitor markedly reduces the relative fluorescence. As a negative control, the reaction is carried out without proteasomes. The reaction carried out according to the method of the invention allows without any problems identification of an inhibition of the proteasome activity and thus identification of inhibitors of the proteasome.

It is also possible to use other inhibitors for testing the method, such as, for example, the abovementioned known inhibitors of proteasome activity.

Figure 4:
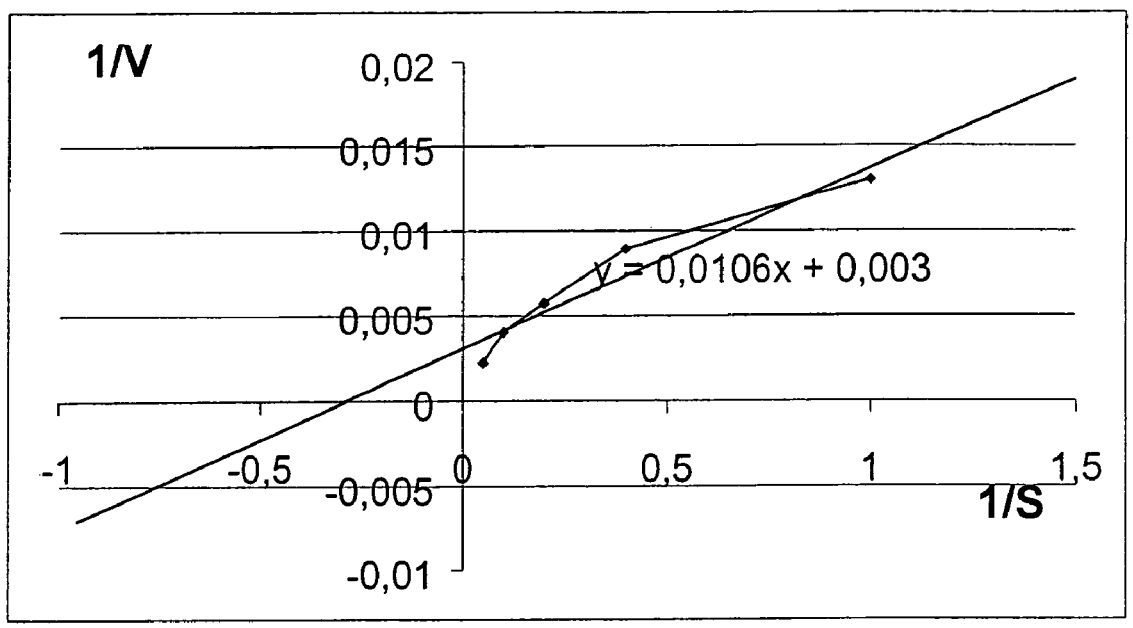
FIG. 4 is a $K_M$ determination for the peptide substrate Suc-LLVY-AMC (SEQ. ID. NO. 1). A constant amount of proteasomes (approx. 70 ng per reaction) was incubated with increasing amounts of substrate and the increase in fluorescence was then determined over a period of 5 minutes. The slopes of the curve (dotted line) were determined by calculating trend lines. Calculation of the $K_M$ for Suc-LLVY-AMC (SEQ. ID. NO. 1) according to Lineweaver-Burke gave a value of 5 μM.

In order to determine optimal conditions for a method for identifying inhibitors of proteasomes or for determining the activity of the polypeptide complexes, it is advantageous to determine the particular $K_M$ value of the substrate used. This value indicates the concentration of the substrate or substrates preferably to be used. The $K_M$ deteremined for the substrate Suc-LLVY-AMC (SEQ. ID. NO. 1) used by way of example was 5 μM (see FIG. 4).

The method of the invention may also be used for identifying inhibitors of the 26S/20S proteasome from other organisms, for example of the human or animal 26S/20S proteasome, i.e. compounds which are used, for example, for cell activation, cell cycle control, cell differentiation and maturation or for inducing apoptosis in humans. This is important with regard to diseases such as, for example, cancer, HIV, allergies, autoimmune diseases, infectious diseases, stroke, in inflammatory processes and in transplant medicine (for this, see WO 00/33654), in which particular enzymic activities of the proteasome play a decisive part. Thus, the method is not limited to identifying inhibitors of the fungal proteasome but may be used in principle for searching for inhibitors of this polypeptide complex from a large variety of organisms.

It is obvious that, in addition to the particularly preferred, above-described method according to the invention for identifying inhibitors of fungal 20S proteasomes and of fungicides, all conventional methods known to the skilled worker may also be used, for example those described in WO 00/23614, Groll et al. (1997), *Nature* 386, 463, Mellgren (1997): *J. Biol. Chem.* 272, 29899, Meng et al. (1999), *PNAS* 96, 10403, McCormack et al. (1998), *Biochemistry* 37, 7792, Driscoll and Goldberg (1990), *J. Biol. Chem.* 265, 4789 or Orlowski et al. (1993): *Biochemistry* 32, 1563 or those which are commercially available (for example from Calbiochem). Examples of proteasome substrates used here are, besides those already described above, also lysozyme, alpha-lactalbumin, beta-lactoglobulin, β-insulin and ornithine decarboxylase. If it is intended to measure the activity of the whole 26S proteasome, the substrate is preferably ubiquitinated or the reaction mixture additionally contains ubiquitin and ubiquitinating enzymes.

It was possible, with the aid of the method described above by way of example, to identify compounds which exhibit a fungicidal action in vivo, in addition to the in-vitro inhibition of 20S proteasomes.

Table I displays, by way of example, compounds which have an inhibitory action in the method of the invention and a fungicidal action in the following in-vivo tests, here, for example, the "agar diffusion assay", on various fungi. In this connection, the following fungi were used by way of example: *Botrytis cinerea* (BOTRCI), *Ustilago maydis* (USTIMA), *Pyricularia oryzae* (PYRIOR), *Fusarium culmorum* (FUSACU), *Rhizoctonia solani* (RHIZSO), *Pseudocercosporella herpotrichoides* (PSDCHW). The "MIC" value describes the "minimum inhibitory concentration". It represents the smallest concentration (in ppm) at which an active compound prevents the fungus from growing. Thus, the lower the MIC value, the higher the efficacy of the substance assayed.

TABLE I

| Example | Compound | Organism | MIC |
|---|---|---|---|
| 1 | Carbobenzoxy-L-leucyl-L-leucyl-L-norvalinal (MG-115) | BOTRCI | 58.6 |
|  |  | FUSACU | >1000 |
|  |  | PSDCHR | >1000 |
|  |  | PYRIOR | 2.0 |
|  |  | RHIZSO | >1000 |
|  |  | USTIMA | 750 |
| 2 | Aprotinin | BOTRCI | 339.3 |
|  |  | FUSACU | >1000 |
|  |  | PSDCHR | >1000 |
|  |  | PYRIOR | 18.0 |
|  |  | RHIZSO | >1000 |
|  |  | USTIMA | 750 |

This demonstrates that the inhibitors of 26S/20S proteasomes, identified with the aid of the method of the invention, and also known inhibitors of the human 26S/20S proteasome are suitable for damaging or destroying fungi.

The agar diffusion assay is a simple way of determining the sensitivity of microorganisms to antimicrobial active compounds (see, for example, Mitchell and Carter (2000): Modeling antimocrobial activity of Clorox™ using an agar-diffusion test: a new twist on an old experiment. *Bioscene* 26(3), 9-13). In this assay, an agar plate inoculated with the microorganism, i.e. in this case the particular fungus, is used and the active compound is enabled to diffuse slowly into the agar medium. This is carried out, for example, by contacting a small round filter impregnated with the said active compound with the agar by placing it, for example, simply on the plate. The concentration of the active compound diffusing through the medium inoculated with the fungus decreases quadratically as a function of the square of the distance covered. After a particular diffusion distance, the active compound is so diluted that it no longer exhibits any action on the fungus. The efficacy of a particular substance is indicated by the development of zones in which growth is inhibited. These zones can be observed as clear regions around the spot from which the active compound has penetrated the agar medium. The diameter of these zones or rings can be measured and used as a measure for the efficacy of the substance.

In addition to the assay mentioned for evaluating the fungicidal efficacy of the 26S/20S proteasome inhibitors in vivo, other methods known to the skilled worker may also be used as long as they make it possible to evaluate a fungicidal or fungistatic action of the compounds assayed.

The present invention therefore also relates to inhibitors of 20S and 26S proteasomes, in particular inhibitors of fungal 20S or 26S proteasomes, and to fungicides found with the aid of the inventive method for identifying inhibitors of 20S and 26S proteasomes.

The present invention likewise relates to the use of inhibitors of the 26S/20S proteasome, in particular of the fungal 26S/20S proteasome, as fungicides. These also include all already known inhibitors of 26S/20S proteasomes from other organisms, such as, for example, the abovementioned inhibitors. Further inhibitors which may be used in a manner according to the invention and which are therefore explicitly included in their entirety in the subject-matter of the present invention are, for example, the proteasome inhibitors mentioned in WO 00/43000, WO 95/24914 and WO 91/13904.

Depending on their particular physical and/or chemical properties, the compounds can be converted to the customary formulations such as solutions, emulsions, suspensions, powders, foams, pastes, granules, aerosols, microencapsulations in polymeric substances and in coating compositions for seeds, and ULV cool and warm fogging formulations for the use in plant protection.

These formulations are produced in a known manner, for example by mixing the active compounds with extenders, that is liquid solvents, liquefied gases under pressure and/or solid carriers, where appropriate by using surfactants, that is emulsifiers and/or dispersants and/or foam formers. If the extender used is water, it is also possible to use, for example, organic solvents as auxiliary solvents. Suitable liquid solvents are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, and water. Liquefied gaseous extenders or carriers mean those liquids which are gaseous at standard temperature and under atmospheric pressure, for example aerosol propellants such as halogenated hydrocarbons and also butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as finely divided silica, alumina and silicates.

Suitable solid carriers for granules are: for example crushed and fractionated natural rocks such as calcite, marble, pumice, sepiolite, dolomite, and also synthetic granules of inorganic and organic meals, and granules of organic materials such as sawdust, coconut shells, maize cobs and tobacco stalks. Suitable emulsifiers and/or foam formers are: for example non-ionogenic and anionic emulsifiers such as polyoxyethylene fatty acid esters, polyoxyethylene fatty alcohol ethers, e.g. alkylaryl polyglycol ethers, alkyl sulphonates, alkyl sulphates, aryl sulphonates, and protein hydrolysates. Suitable dispersants are: for example lignosulphite waste liquors and methylcellulose.

Tackifiers such as carboxymethylcellulose and natural and synthetic polymers in the form of powders, granules or latices, such as gum arabic, polyvinyl alcohol, polyvinyl acetate, and natural phospholipids such as cephalins and lecithins, and synthetic phospholipids can be used in the formulations. Other possible additives are mineral and vegetable oils.

It is possible to use colorants such as inorganic pigments, for example iron oxide, titanium oxide, Prussian Blue, and organic dyes such as alizarin dyes, azo dyes and metal phthalocyanine dyes, and trace nutrients such as salts of iron, manganese, boron, copper, cobalt, molybdenum and zinc.

The formulations generally contain between 0.1 and 95% by weight of active compound, preferably between 0.5 and 90%.

The active compounds or their formulations may be contacted directly with the fungi to be controlled or the habitat thereof.

EXAMPLES

Example 1

Preparation of the Proteasome Extract from *S. Cerevisiae* Cells 150 ml of compact fermenter yeast were resuspended with 250 ml of buffer (50 mM Tris-HCl, pH 7.5; 10 mM EDTA) to give 400 ml of a yeast suspension. The cells were disrupted in three runs in a high-pressure homogenizer under a pressure of 1800 psi and at 27° C. After cell disruption, the pH was adjusted to 7.5 using 0.1 M NaOH. Immediately thereafter, the incubation was carried out at 60° C. for 60 minutes. The suspension was then centrifuged three times at 13 000 rpm in a JA20 rotor at 4° C. in order to remove the precipitated components. It was then possible to use a 1:100 dilution of the remaining supernatant which contains the proteasomes immediately in the assay for identifying inhibitors.

Since the activity can vary, depending on the state of fermentation of the cells, it is recommended to determine the activity of the proteasomes beforehand in order to be able to choose the appropriate dilution.

Example 2

Preparation of the Proteasome Extract from *U. Maydis* Cells

Protoplasts were prepared from 50 ml of an *U. maydis* culture according to Schulz et al. (Schulz et al. (1990), The b alleles of *Ustilago maydis*, whose combinations program pathogenic development, code for polypeptides containing a homeodomain-related motif. *Cell* 60, 295-306). This was followed by pelleting the protoplasts at 2000 rpm for 5 min. Subsequently, the protoplasts were made to burst by adding 50 µl of buffer (50 mM Tris-HCl, pH 7.5; 10 mM EDTA), due to the altered osmotic conditions. Cell debris was pelleted by centrifugation at 13 000 rpm for 5 min. The supernatant was again incubated at 60° C. for 1 h followed by pelleting of the denatured proteins at 13 000 rpm for 5 min. The following activity test of the *U. maydis* proteasomes obtained determines the dilution to be used for the subsequent assay.

Example 3

Assay System Check Using the Known Inhibitor MG-132 (Activity Assay)

The activity and inhibition assay which makes use of the known inhibitor MG-132 from Calbiochem and which is intended to check the usability of the method of the invention was carried out in 384-well MTPs (microtitre plates with 384 wells). A total volume of 50 µl per well contained 25 µl of enzyme buffer (10 mM Tris-HCl, 2 mM EDTA) containing the proteasomes (2.8 mg), 20 µl substrate solution (13 µM Suc-LLVY-AMC (SEQ. ID. NO. 1), 0.06% SDS, 10% DMSO, 10 mM Tris-HCl, pH 7.5; 2 mM EDTA) containing the substrate and 5 µl of the test substance (160 nN MG-132 in 5% DMSO). The preliminary measurement (fluorescence) was carried out at 360/465 nm (35 nm bandwidth). The incubation was carried out at 25° C. for 40 minutes. The fluorescence was measured again at 360/465 nm (35 nm bandwidth).

Example 4

Identification of Inhibitors of the Proteasome (Screening)

384-well MTPs from Greiner were used for the proteasome inhibition assay in the UHTS (screening). The test substances were introduced first in 5 µl of test substance solution (50 mM Tris-HCl, pH 7.5; 10 mM EDTA) so that the final concentration of the test substances in the inhibition assay was 2 µM. A negative control of 5 µl (160 nM MG-132; 5% DMSO) and a positive control of 5 µl (5% DMSO) were applied to additional wells on the plate. 20 µl of the substrate solution (13 µM Suc-LLVY-AMC; 0.06% SDS; 10% (v/v) DMSO; 10 mM Tris-HCl, pH 7.5; 2 mM EDTA) were added to the test substance solution. This was followed by adding 25 µl of enzyme solution (10 mM Tris-HCl, pH 7.5; 2 mM EDTA; 280 ng of proteasomes per well) and determining relative fluorescence (preliminary measurement at 360/465 nm, bandwidth 25 nm). After incubating at 25° C. for 40 min, relative fluorescence was measured again at 360/465 nm, bandwidth 25 nm.

Example 5

Identification of Inhibitors of the Proteasome (Screening)

384-well MTPs from Greiner were used for the proteasome-inhibition assay in the UHTS (screening). The test substances were initially introduced in 5 µl of test substance solution (50 mM Tris-HCl, pH 7.5; 10 mM EDTA) in 352 wells so that the final concentration of the test substances in the inhibition assay was 2 µM. For a negative control (32 wells) and a positive control (32 wells), in each case 5 µl of 5% DMSO were applied to additional wells on the plate. 20 µl of the substrate solution (13 µM Suc-LLVY-AMC (SEQ. ID. NO. 1); 0.06% SDS; 10% (v/v) DMSO; 10 mM Tris-HCl, pH 7.5; 2 mM EDTA) were added to the test substance solution. This was followed by adding 25 µl of enzyme solution (10 mM Tris-HCl, pH 7.5; 2 mM EDTA; proteasome extract 1:100, corresponding to 280 ng/well), adding only buffer without enzyme for the negative control. Subsequently, fluorescence was first measured in a preliminary measurement at an excitation wavelength of 360 nm and an emission wavelength of 460 nm (preliminary measurement at 360/465 nm, bandwidth 25 nm). This was followed by incubating the MTPs at 37° C. for at least 40 min and, subsequently, determining fluorescence as described above.

REFERENCES

1. Bogyo, M., Shin, S., McMaster, J. S. & Ploegh, H. L. (1998), *Chem. Biol.* 5, 307-320.
2. Coux et al. (1995), *Ann. Rev. Biochem.* 65, 801-847.
3. Coux et al. (1998), *J. Biol. Chem.* 273(15), 8820-8828.
4. Driscoll und Goldberg (1990), *J. Biol. Chem.* 265, 4789.
5. EP 0 345 750
6. Fenteany et al. (1995), *Science,* 268, 726-731.
7. Groll et al. (1997), *Nature* 386, 463-471.
8. JP 05292964
9. JP 06022759

10. Klafky et al. (1995), *Neuroscience Letters* 201, 29-32.
11. Knowlton et al. (1997), *Nature* 390, 639-643.
12. Kroll et al. (1999), *Chem. Biol.* 6, 889-698.
13. Lee und Goldberg (1989), *J. Biol. Chem.* 271, 27280.
14. Lee und Goldberg (1998), *Molecular and Cellular Biology* 18, 30-38.
15. McCormack et al. (1998), *Biochemistry* 37, 7792-7800.
16. Mellgren (1997), *J. Biol. Chem.* 272(47), 29899-29903.
17. Meng et al. (1999), *PNAS* 96, 10403.
18. Mitchell und Carter (2000), *Bioscene* 26(3), 9-13.
19. Orlowski et al. (1993), *Biochemistry* 32, 1563.
20. Schulz et al. (1990), *Cell* 60, 295-306.
21. Stack et al. (2000), *Nature Biotechnology* 18, 1298-1302.
22. Stein et al. (1996), *Biochemistry* 35, 3899.
23. WO 00/23614
24. WO 00/33654
25. WO 00/43000
26. WO 91/13904
27. WO 95/24914
28. WO 98/42829
29. Zhang et al. (1999), *J. Biomol. Screen.* 4(2):67-73).

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A method for identifying a fungicide comprising:
   (a) contacting a candidate compound with fungal 20S proteasomes in the presence of a substrate of the fungal 20S proteasomes and in the presence of from 2 to 10% (v/v) dimethyl sulphoxide,
   (b) selecting those candidate compounds which specifically inhibit an enzymatic conversion of the substrate by the fungal 20S proteasomes, and
   (c) testing for the fungicidal action of those candidate compounds on fungi in an in vivo assay.

2. The method according to claim 1 wherein said method is a high throughput screening assay.

* * * * *